US011998237B2

(12) United States Patent
Lindekugel et al.

(10) Patent No.: US 11,998,237 B2
(45) Date of Patent: Jun. 4, 2024

(54) INTRAOSSEOUS DEVICE INCLUDING A SENSING OBTURATOR

(71) Applicant: Bard Access Systems, Inc., Salt Lake City, UT (US)

(72) Inventors: Eric W. Lindekugel, Salt Lake City, UT (US); Daniel Pett, Sandy, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 123 days.

(21) Appl. No.: 17/337,100

(22) Filed: Jun. 2, 2021

(65) Prior Publication Data

US 2021/0378707 A1    Dec. 9, 2021

Related U.S. Application Data

(60) Provisional application No. 63/034,338, filed on Jun. 3, 2020.

(51) Int. Cl.
*A61B 17/34* (2006.01)
*A61B 90/98* (2016.01)
(Continued)

(52) U.S. Cl.
CPC .......... *A61B 17/3472* (2013.01); *A61B 90/98* (2016.02); *A61B 2017/00026* (2013.01);
(Continued)

(58) Field of Classification Search
CPC .......... A61B 2017/00026; A61B 2017/00035; A61B 2017/00084; A61B 2090/064;
(Continued)

(56) References Cited

U.S. PATENT DOCUMENTS 2,773,501 A    12/1956  Young
3,071,135 A    1/1963   Baldwin et al.
(Continued)

FOREIGN PATENT DOCUMENTS

CN    108742795 A    11/2018
CN    110547847 A    12/2019
(Continued)

OTHER PUBLICATIONS

PCT/US2022/014391 filed Jan. 28, 2022 International Search Report and Written Opinion dated Apr. 14, 2022.
(Continued)

*Primary Examiner* — Larry E Waggle, Jr.
(74) *Attorney, Agent, or Firm* — Rutan & Tucker LLP (57) ABSTRACT

Disclosed herein are medical device systems, and methods thereof, for automatically detecting access to a medullary cavity. Embodiments include intraosseous access systems with sensing obturators, configured to detect a change in modality, e.g. pressure, oxygen saturation, electrical impedance, etc. at a distal tip thereof. Signals can be transmitted to a control logic that can modify the activation of a driver in response. Signals can be transmitted by way of wired or wireless communication. In an embodiment, signals can be transmitted through conductive polymer material that forms the obturator and allows the obturator to be flexible enough to mitigate accidental needle stick injuries.

16 Claims, 5 Drawing Sheets

(51) Int. Cl.
  *A61B 17/00* (2006.01)
  *A61B 90/00* (2016.01)
(52) U.S. Cl.
  CPC ............... *A61B 2017/00035* (2013.01); *A61B 2017/00084* (2013.01); *A61B 2090/064* (2016.02); *A61B 2090/065* (2016.02)
(58) Field of Classification Search
  CPC .............. A61B 2090/065; A61B 17/16; A61B 17/1604; A61B 17/3472; A61B 17/3494; A61B 17/3496
  See application file for complete search history.

(56) References Cited

U.S. PATENT DOCUMENTS

| | | | |
|---|---|---|---|
| 3,734,207 A | 5/1973 | Fishbein | |
| 3,804,544 A | 4/1974 | Adams | |
| 3,811,442 A | 5/1974 | Maroth | |
| 3,815,605 A | 6/1974 | Schmidt et al. | |
| 3,991,765 A | 11/1976 | Cohen | |
| 4,266,555 A | 5/1981 | Jamshidi | |
| 4,314,565 A | 2/1982 | Lee | |
| 4,381,777 A | 5/1983 | Garnier | |
| 4,383,530 A | 5/1983 | Bruno | |
| 4,736,742 A | 4/1988 | Alexson et al. | |
| 4,787,893 A | 11/1988 | Villette | |
| 4,889,529 A | 12/1989 | Haindl | |
| 4,952,207 A | 8/1990 | Lemieux | |
| 4,964,854 A | 10/1990 | Luther | |
| 4,969,870 A | 11/1990 | Kramer et al. | |
| 5,040,542 A | 8/1991 | Gray | |
| 5,042,558 A | 8/1991 | Hussey et al. | |
| 5,053,017 A | 10/1991 | Chamuel | |
| 5,122,114 A | 6/1992 | Miller et al. | |
| 5,207,697 A | 5/1993 | Carusillo et al. | |
| 5,263,939 A | 11/1993 | Wortrich | |
| 5,290,267 A | 3/1994 | Zimmermann | |
| 5,312,364 A | 5/1994 | Jacobs | |
| 5,332,398 A | 7/1994 | Miller et al. | |
| 5,364,367 A | 11/1994 | Banks et al. | |
| 5,372,583 A | 12/1994 | Roberts et al. | |
| 5,406,940 A | 4/1995 | Melzer et al. | |
| 5,451,210 A | 9/1995 | Kramer et al. | |
| 5,554,154 A | 9/1996 | Rosenberg | |
| 5,575,780 A | 11/1996 | Saito | |
| 5,591,188 A | 1/1997 | Waisman | |
| 5,601,559 A | 2/1997 | Melker et al. | |
| 5,667,509 A | 9/1997 | Westin | |
| 5,688,249 A | 11/1997 | Chang et al. | |
| 5,779,708 A | 7/1998 | Wu | |
| 5,817,052 A | 10/1998 | Johnson et al. | |
| 5,853,393 A | 12/1998 | Bogert | |
| 5,868,711 A | 2/1999 | Kramer et al. | |
| 5,885,293 A | 3/1999 | McDevitt | |
| 5,927,976 A | 7/1999 | Wu | |
| 5,960,797 A | 10/1999 | Kramer et al. | |
| 5,967,143 A | 10/1999 | Klappenberger | |
| 6,056,165 A | 5/2000 | Speranza | |
| 6,104,162 A | 8/2000 | Sainsbury et al. | |
| 6,117,108 A | 9/2000 | Woehr et al. | |
| 6,135,769 A | 10/2000 | Kwan | |
| 6,159,161 A | 12/2000 | Hodosh | |
| 6,199,664 B1 | 3/2001 | Tkaczyk et al. | |
| 6,210,373 B1 | 4/2001 | Allmon | |
| 6,228,088 B1 | 5/2001 | Miller et al. | |
| 6,247,928 B1 | 6/2001 | Meller et al. | |
| 6,270,484 B1 * | 8/2001 | Yoon .................. | A61B 17/3494 604/264 |
| 6,273,715 B1 | 8/2001 | Meller et al. | |
| 6,419,490 B1 | 7/2002 | Kitchings Weathers, Jr. | |
| 6,458,117 B1 | 10/2002 | Pollins, Sr. | |
| 6,527,778 B2 | 3/2003 | Athanasiou et al. | |
| 6,547,561 B2 | 4/2003 | Meller et al. | |
| 6,602,214 B2 | 8/2003 | Heinz et al. | |
| 6,626,887 B1 | 9/2003 | Wu | |
| 6,629,959 B2 | 10/2003 | Kuracina et al. | |
| 6,641,395 B2 | 11/2003 | Kumar et al. | |
| 6,652,490 B2 | 11/2003 | Howell | |
| 6,692,471 B2 | 2/2004 | Boudreaux | |
| 6,761,726 B1 | 7/2004 | Findlay et al. | |
| 6,814,734 B2 | 11/2004 | Chappuis et al. | |
| 6,830,562 B2 | 12/2004 | Mogensen et al. | |
| 6,875,219 B2 | 4/2005 | Arramon et al. | |
| 6,905,486 B2 | 6/2005 | Gibbs | |
| 6,916,292 B2 | 7/2005 | Morawski et al. | |
| 6,984,213 B2 | 1/2006 | Horner et al. | |
| 6,997,907 B2 | 2/2006 | Safabash et al. | |
| 7,112,191 B2 | 9/2006 | Daga | |
| 7,135,031 B2 | 11/2006 | Flint | |
| 7,214,208 B2 | 5/2007 | Vaillancourt et al. | |
| 7,347,838 B2 | 3/2008 | Kulli | |
| 7,347,840 B2 | 3/2008 | Findlay et al. | |
| 7,407,493 B2 | 8/2008 | Cane' | |
| 7,458,954 B2 | 12/2008 | Ferguson et al. | |
| 7,513,888 B2 | 4/2009 | Sircom et al. | |
| 7,530,965 B2 | 5/2009 | Villa et al. | |
| 7,534,227 B2 | 5/2009 | Kulli | |
| 7,569,033 B2 | 8/2009 | Greene et al. | |
| 7,582,102 B2 | 9/2009 | Heinz et al. | |
| 7,588,559 B2 | 9/2009 | Aravena et al. | |
| 7,658,725 B2 | 2/2010 | Bialecki et al. | |
| 7,670,328 B2 * | 3/2010 | Miller ................ | A61B 17/1622 606/167 |
| 7,699,807 B2 | 4/2010 | Faust et al. | |
| 7,699,850 B2 | 4/2010 | Miller | |
| 7,736,332 B2 | 6/2010 | Carlyon et al. | |
| 7,749,225 B2 | 7/2010 | Chappuis et al. | |
| 7,798,994 B2 | 9/2010 | Brimhall | |
| 7,811,260 B2 | 10/2010 | Miller et al. | |
| 7,815,642 B2 | 10/2010 | Miller | |
| 7,828,774 B2 | 11/2010 | Harding et al. | |
| 7,833,204 B2 | 11/2010 | Picha | |
| 7,842,038 B2 | 11/2010 | Haddock et al. | |
| 7,850,620 B2 | 12/2010 | Miller et al. | |
| 7,850,650 B2 | 12/2010 | Breitweiser | |
| D633,199 S | 2/2011 | MacKay et al. | |
| 7,899,528 B2 | 3/2011 | Miller et al. | |
| 7,905,857 B2 | 3/2011 | Swisher | |
| 7,951,089 B2 | 5/2011 | Miller | |
| 7,955,297 B2 | 6/2011 | Radmer et al. | |
| 7,972,339 B2 | 7/2011 | Nassiri et al. | |
| 7,976,502 B2 | 7/2011 | Baid | |
| 8,038,664 B2 | 10/2011 | Miller et al. | |
| 8,043,253 B2 | 10/2011 | Kraft et al. | |
| 8,043,265 B2 | 10/2011 | Abe et al. | |
| 8,142,365 B2 | 3/2012 | Miller | |
| 8,152,771 B2 | 4/2012 | Mogensen et al. | |
| 8,162,904 B2 | 4/2012 | Takano et al. | |
| 8,167,899 B2 | 5/2012 | Justis et al. | |
| 8,235,945 B2 | 8/2012 | Baid | |
| 8,246,584 B2 | 8/2012 | Aravena et al. | |
| 8,273,053 B2 | 9/2012 | Saltzstein | |
| 8,292,891 B2 | 10/2012 | Browne et al. | |
| 8,308,693 B2 | 11/2012 | Miller et al. | |
| 8,333,769 B2 | 12/2012 | Browne et al. | |
| 8,356,598 B2 | 1/2013 | Rumsey | |
| 8,357,163 B2 | 1/2013 | Sidebotham et al. | |
| 8,388,541 B2 | 3/2013 | Messerly et al. | |
| 8,388,623 B2 | 3/2013 | Browne et al. | |
| 8,414,539 B1 | 4/2013 | Kuracina et al. | |
| 8,419,683 B2 | 4/2013 | Miller et al. | |
| 8,480,632 B2 | 7/2013 | Miller et al. | |
| 8,480,672 B2 | 7/2013 | Browne et al. | |
| 8,486,027 B2 | 7/2013 | Findlay et al. | |
| 8,506,568 B2 | 8/2013 | Miller | |
| 8,535,271 B2 | 9/2013 | Fuchs et al. | |
| 8,562,615 B2 | 10/2013 | Browne et al. | |
| 8,641,715 B2 | 2/2014 | Miller | |
| 8,647,257 B2 | 2/2014 | Jansen et al. | |
| 8,656,929 B2 | 2/2014 | Miller et al. | |
| 8,657,790 B2 | 2/2014 | Tal et al. | |
| 8,663,231 B2 | 3/2014 | Browne et al. | |
| 8,668,698 B2 | 3/2014 | Miller et al. | |

(56) References Cited

U.S. PATENT DOCUMENTS

| | | |
|---|---|---|
| 8,684,978 B2 | 4/2014 | Miller et al. |
| 8,690,791 B2 | 4/2014 | Miller |
| 8,715,287 B2 | 5/2014 | Miller |
| 8,771,230 B2 | 7/2014 | White et al. |
| 8,781,555 B2 | 7/2014 | Burnside et al. |
| 8,801,663 B2 | 8/2014 | Woehr |
| 8,812,101 B2 | 8/2014 | Miller et al. |
| 8,814,835 B2 | 8/2014 | Baid |
| 8,821,493 B2 | 9/2014 | Anderson |
| 8,828,001 B2 | 9/2014 | Stearns et al. |
| 8,849,382 B2 | 9/2014 | Cox et al. |
| 8,870,872 B2 | 10/2014 | Miller |
| 8,894,654 B2 | 11/2014 | Anderson |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 | 4/2017 | Nino et al. |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 10,052,111 B2 | 8/2018 | Miller et al. |
| 10,092,320 B2 | 10/2018 | Morgan et al. |
| 10,092,706 B2 | 10/2018 | Denzer et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| D898,908 S | 10/2020 | Denzer et al. |
| 10,893,887 B2 | 1/2021 | Blanchard |
| 10,973,532 B2 | 4/2021 | Miller et al. |
| 10,973,545 B2 | 4/2021 | Miller et al. |
| 10,980,522 B2 | 4/2021 | Muse |
| 11,298,202 B2 | 4/2022 | Miller et al. |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2005/0165403 A1 | 7/2005 | Miller |
| 2006/0015066 A1 | 1/2006 | Turieo et al. |
| 2006/0025723 A1 | 2/2006 | Ballarini |
| 2006/0058826 A1 | 3/2006 | Evans et al. |
| 2007/0049945 A1 | 3/2007 | Miller |
| 2007/0191772 A1 | 8/2007 | Wojcik |
| 2007/0270775 A1 | 11/2007 | Miller et al. |
| 2007/0276352 A1 | 11/2007 | Crocker et al. |
| 2007/0282344 A1 | 12/2007 | Yedlicka et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0194446 A1 | 8/2009 | Miller et al. |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0174243 A1 | 7/2010 | McKay |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0202065 A1 | 8/2011 | Takizawa et al. |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0171873 A1* | 6/2014 | Mark ................. A61B 17/3417 604/164.01 |
| 2014/0188133 A1 | 7/2014 | Misener |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | Bin Abdulla |

(56) References Cited

U.S. PATENT DOCUMENTS

| | | |
|---|---|---|
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2015/0367487 A1 | 12/2015 | Nino et al. |
| 2016/0022282 A1 | 1/2016 | Miller et al. |
| 2016/0022284 A1 | 1/2016 | Lele et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0305497 A1 | 10/2016 | Victor et al. |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |
| 2018/0049772 A1 | 2/2018 | Brockman et al. |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0153474 A1* | 6/2018 | Aeschlimann ........ A61N 1/0502 |
| 2018/0154112 A1 | 6/2018 | Chan et al. |
| 2018/0221003 A1 | 8/2018 | Hibner et al. |
| 2018/0228509 A1 | 8/2018 | Fojtik |
| 2018/0242982 A1 | 8/2018 | Laughlin et al. |
| 2019/0059986 A1* | 2/2019 | Shelton, IV ........ A61B 18/1447 |
| 2019/0069812 A1* | 3/2019 | Isaacson ................. A61B 5/01 |
| 2019/0083753 A1 | 3/2019 | Chu |
| 2019/0175220 A1* | 6/2019 | Coppedge .......... A61B 17/1671 |
| 2019/0282244 A1 | 9/2019 | Muse |
| 2020/0054347 A1 | 2/2020 | Coppedge et al. |
| 2020/0054410 A1 | 2/2020 | Pfotenhauer et al. |
| 2020/0113584 A1 | 4/2020 | McGinley et al. |
| 2020/0129186 A1 | 4/2020 | Miller et al. |
| 2020/0197121 A1 | 6/2020 | Morey et al. |
| 2020/0297382 A1 | 9/2020 | Coppedge et al. |
| 2020/0297452 A1 | 9/2020 | Coppedge et al. |
| 2020/0337782 A1* | 10/2020 | Glassman ............... A61B 90/37 |
| 2021/0093357 A1 | 4/2021 | Pett et al. |
| 2021/0093358 A1 | 4/2021 | Lindekugel et al. |
| 2021/0282812 A1 | 9/2021 | Tierney et al. |
| 2021/0322055 A1 | 10/2021 | Lindekugel et al. |
| 2021/0375445 A1 | 12/2021 | Lindekugel et al. |
| 2022/0240976 A1 | 8/2022 | Pett et al. |
| 2022/0249104 A1 | 8/2022 | Pett et al. |
| 2023/0106545 A1 | 4/2023 | Pett et al. |
| 2023/0285049 A1 | 9/2023 | Howell |
| 2023/0414251 A1 | 12/2023 | Pett et al. |

FOREIGN PATENT DOCUMENTS

| | | |
|---|---|---|
| EP | 0923961 A1 | 6/1999 |
| ES | 2390297 A1 | 11/2012 |
| FR | 2581548 A1 | 11/1986 |
| JP | 2018509969 A | 4/2018 |
| KR | 20090006621 A | 1/2009 |
| WO | 1997024151 A1 | 7/1997 |
| WO | 1998052638 A3 | 2/1999 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011070593 A1 | 6/2011 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014075165 A1 | 5/2014 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 2016033016 A1 | 3/2016 |
| WO | 16053834 A1 | 4/2016 |
| WO | 2016/085973 A1 | 6/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019/164990 A1 | 8/2019 |
| WO | 2021/011795 A1 | 1/2021 |
| WO | 2021/016122 A1 | 1/2021 |
| WO | 2021/062385 A1 | 4/2021 |
| WO | 2021062038 A1 | 4/2021 |
| WO | 2021062394 A1 | 4/2021 |
| WO | 2022/165232 A1 | 8/2022 |
| WO | 2022/170269 A1 | 8/2022 |

OTHER PUBLICATIONS

PCT/US2022/015686 filed Feb. 8, 2022 International Search Report and Written Opinion dated May 25, 2022.

U.S. Appl. No. 17/031,650, filed Sep. 24, 2020 Final Office Action dated Jul. 20, 2022.

U.S. Appl. No. 17/031,650, filed Sep. 24, 2020 Notice of Allowance dated Oct. 12, 2022.

U.S. Appl. No. 17/035,336, filed Sep. 28, 2020 Restriction Requirement dated Jul. 26, 2022.

U.S. Appl. No. 17/035,272, filed Sep. 28, 2020 Non-Final Office Action dated Mar. 9, 2023.

U.S. Appl. No. 17/035,272, filed Sep. 28, 2020 Restriction Requirement dated Dec. 9, 2022.

U.S. Appl. No. 17/035,336, filed Sep. 28, 2020 Notice of Allowance dated Jan. 11, 2023.

U.S. Appl. No. 17/235,134, filed Apr. 20, 2021 Restriction Requirement dated Mar. 7, 2023.

Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.

(56) References Cited

OTHER PUBLICATIONS

PCT/US2019/ 018828 filed Feb. 20, 2019 International Preliminary Report on Patentability dated Aug. 27, 2020.
PCT/US2019/ 018828 filed Feb. 20, 2019 International Search Report and Written Opinion dated Jun. 13, 2019.
PCT/US2020/ 053119 filed Sep. 28, 2020 International Search Report and Written Opinion dated Jan. 5, 2021.
PCT/US2020/052558 filed Sep. 24, 2020 International Search Report and Written Opinion dated Feb. 11, 2021.
PCT/US2020/053135 filed Sep. 28, 2020 International Search Report and Written Opinion dated Dec. 18, 2020.
PCT/US2021/ 035232 filed Jun. 1, 2021 International Search Report and Written Opinion dated Oct. 19, 2021.
PCT/US2021/028114 filed Apr. 20, 2021 International Search Report and Written Opinion dated Jul. 12, 2021.
PCT/US2021/035475 filed Jun. 2, 2021 International Search Report and Written Opinion dated Sep. 17, 2021.
U.S. Appl. No. 17/031,650, filed Sep. 24, 2020 Non-Final Office Action dated Jan. 19, 2022.
PCT/US2021/ 046573 filed Aug. 18, 2021 International Search Report and Written Opinion dated Nov. 30, 2021.
PCT/US2021/ 047378 filed Aug. 24, 2021 International Search Report and Written Opinion dated Nov. 17, 2021.
PCT/US2021/ 048542 filed Aug. 31, 2021 International Search Report and Written Opinion dated Dec. 9, 2021.
PCT/US2021/ 049475 filed Sep. 8, 2021 International Search Report and Written Opinion dated Dec. 9, 2021.
EP 19757667.1 filed Sep. 18, 2020 Extended European Search Report dated Oct. 22, 2021.
EP 20867024.0 filed Apr. 21, 2022 Extended European Search Report dated Aug. 8, 2023.
EP 20868351.6 filed Apr. 21, 2022 Extended European Search Report dated Aug. 10, 2023.
EP 23166984.7 filed Apr. 6, 2023 Extended European Search Report dated Jul. 5, 2023.
PCT/US2023/015127 filed Mar. 13, 2023 International Search Report and Written Opinion dated Jun. 26, 2023.
U.S. Appl. No. 17/035,272, filed Sep. 28, 2020 Notice of Allowance dated Jul. 7, 2023.
U.S. Appl. No. 17/235,134, filed Apr. 20, 2021 Non-Final Office Action dated Jun. 27, 2023.
U.S. Appl. No. 17/335,870, filed Jun. 1, 2021 Restriction Requirement dated Jul. 25, 2023.
U.S. Appl. No. 17/667,291, filed Feb. 8, 2022 Restriction Requirement dated May 31, 2023.
U.S. Appl. No. 17/235,134, filed Apr. 20, 2021 Notice of Allowance dated Sep. 20, 2023.
U.S. Appl. No. 17/469,613, filed Sep. 8, 2021 Restriction Requirement dated Oct. 23, 2023.
U.S. Appl. No. 17/667,291, filed Feb. 8, 2022 Non-Final Office Action dated Aug. 31, 2023.
U.S. Appl. No. 17/469,613, filed Sep. 8, 2021 Non-Final Office Action dated Jan. 19, 2024.
U.S. Appl. No. 17/863,898, filed Jul. 13, 2022 Final Office Action dated Nov. 22, 2023.

* cited by examiner

INTRAOSSEOUS DEVICE INCLUDING A SENSING OBTURATOR

PRIORITY

This application claims priority to U.S. Provisional Application No. 63/034,338, filed Jun. 3, 2020, which is incorporated by reference in its entirety into this application.

SUMMARY

Embodiments disclosed herein are directed to intraosseous (10) access devices including sensing obturators configured to automatically detect access to a medullary cavity and modify the activation of the drill. Intraosseous access devices often require training to ensure correct placement of the access device. Users must apply sufficient distal driving force to penetrate the bone without applying too much driving force that can result in "back walling" where a needle penetrates a far wall of the bone. Further complications can arise when accessing bones of different sizes and density depending on the age and health of the patient. Moreover, 10 access devices are often used in emergency situations where delays can be critical and fully trained users may not always be available.

Disclosed herein is an obturator configured for use with an intraosseous access system including, an obturator, and a sensor disposed proximate a distal end of the obturator, the sensor configured to detect a change in modality to determine access to a medullary cavity.

In some embodiments, the sensor includes one of a pressure transducer, an oxygen saturation sensor, an electrical impedance sensor, a temperature sensor, or a pH sensor. The sensor is communicatively coupled with a control logic disposed in a driver of the intraosseous access system, the control logic configured to modify operation of the driver when the sensor detects the change in modality. The obturator further includes a sensor interface disposed at a proximal end of the obturator hub and configured to both rotatably and communicatively couple the sensor with the control logic. The obturator includes one of an electrically conductive or an optically conductive thermoplastic configured to communicatively couple the sensor with the sensor interface. The obturator includes a wire extending axially therethrough and configured to communicatively couple the sensor with the sensor interface. The obturator is configured to be disposed within a needle, and wherein the sensor is disposed proximate a distal end of the needle.

In some embodiments, the obturator further includes a second sensor configured to detect a second modality configured to determine access to the medullary cavity. The second sensor includes one of a pressure transducer, an oxygen saturation sensor, an electrical impedance sensor, a temperature sensor, or a pH sensor. The sensor includes a passive RFID chip, and wherein the control logic is configured to provide an interrogation signal configured to induce a response signal from the passive RFID chip to determine access to a medullary cavity.

Also disclosed is a method of detecting access to an internal cavity including, providing an elongate medical device including a sensor disposed at a distal end thereof, urging the elongate medical device through a first tissue, detecting a first modality level, accessing the internal cavity, detecting a change in modality level from the first modality level to determine access to the internal cavity, and communicating the change in modality level to a control logic.

In some embodiments, the elongate medical device includes an obturator configured to be disposed within an intraosseous access needle, and wherein the first tissue is a bone cortex and the internal cavity is a medullary cavity. The sensor includes one of a pressure transducer, an oxygen saturation sensor, an electrical impedance sensor, a temperature sensor, or a pH sensor. The control logic is disposed within an intraosseous access driver releasably coupled to the elongate medical device. The control logic is configured to modify operation of the intraosseous access driver when the sensor detects the change in modality level.

In some embodiments, the obturator further includes a sensor interface disposed at a proximal end thereof and configured to engage the driver and communicatively and rotatably couple the sensor and the control logic. The obturator includes an electrically conductive thermoplastic configured to communicatively couple the sensor with the sensor interface. The medical device includes a wire extending axially therethrough and configured to communicatively couple the sensor with the sensor interface. In some embodiments, the method further includes detecting a change in a second modality level to determine access to the internal cavity and communicating the change in the second modality level to the control logic. The sensor includes a passive RFID chip, and wherein the control logic is configured to provide an interrogation signal configured to induce a response signal from the passive RFID chip to determine access to a medullary cavity.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

As shown in FIG. 1, and to assist in the description of embodiments described herein, a longitudinal axis extends substantially parallel to an axial length of a needle 204 extending from the driver 101. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Figure 1A:
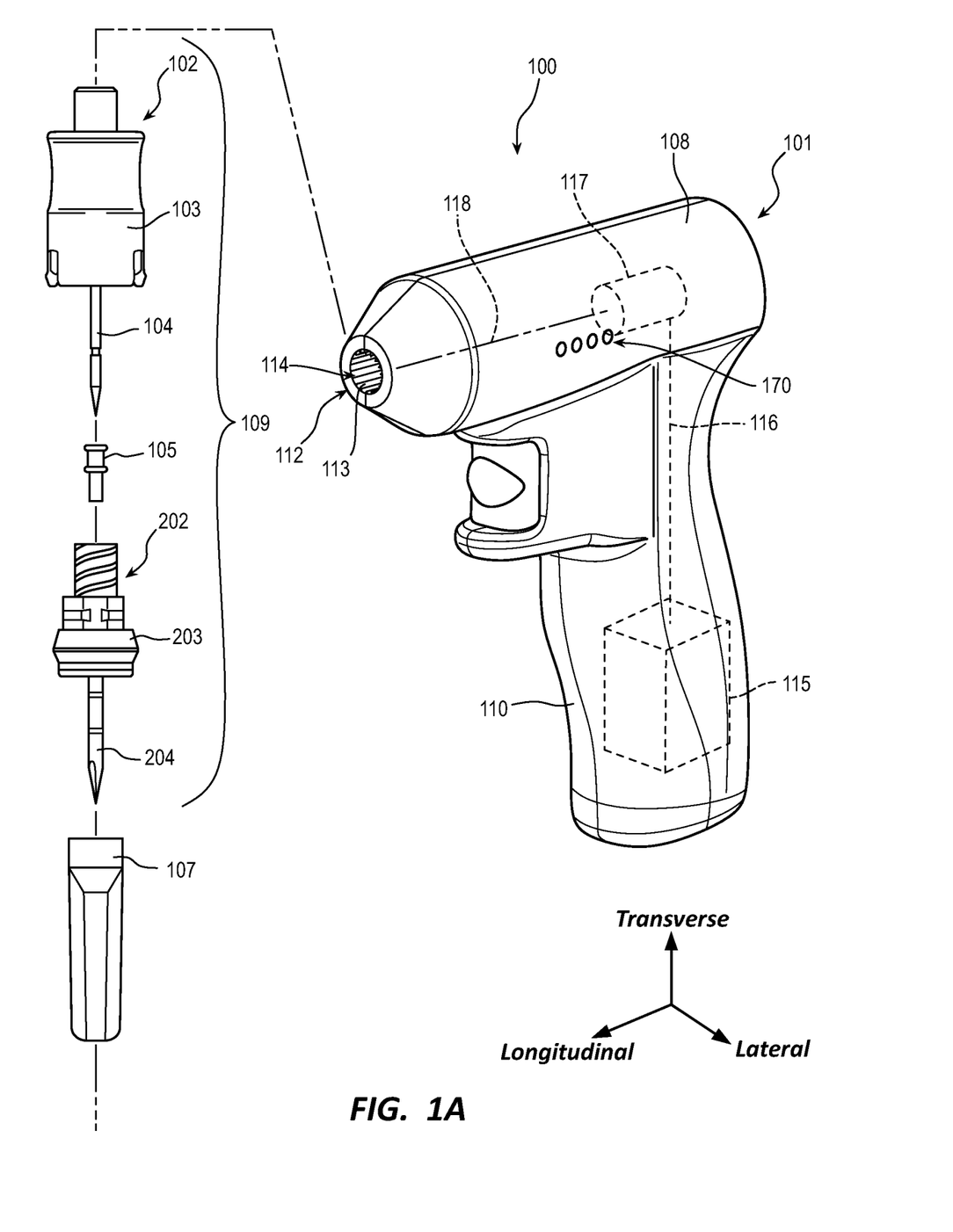
FIG. 1A illustrates an exploded view of an embodiment of an intraosseous access medical device system, wherein an access assembly subset of the system is depicted slightly enlarged and in elevation, and an automated driver component is depicted in perspective, in accordance with embodiments disclosed herein.

The present disclosure relates generally to intraosseous (IO) access device systems that includes a sensing obturator configured to detect access to a medullary cavity. FIG. 1A shows an exploded view of an exemplary intraosseous access system ("system") 100, with some components thereof shown in elevation and another shown in perspective. In an embodiment, the intraosseous access system 100 can be used to penetrate skin surface tissue layers 70 and underlying hard bone, i.e. bone cortex 80, for intraosseous access, such as, for example to access the marrow of the bone and/or a vasculature of the patient via a pathway through an interior of the bone, i.e. the medullary cavity 90.

As used herein, an "access event" includes accessing the medullary cavity 90 with an intraosseous access system 100.

In an embodiment, the system 100 includes a driver 101 and an access assembly 109. The driver 101 can be used to rotate the access assembly 109 and "drill" a needle 204 into the bone of a patient. In embodiments, the driver 101 can be automated or manual. As shown, the driver 101 is an automated driver 101. For example, the automated driver 101 can be a drill that achieves high rotational speeds. In an embodiment, the intraosseous access system 100 can further include an obturator assembly 102, a safety shield ("shield") 105, and a needle assembly 202, which may be referred to, collectively, as the access assembly 109. The needle assembly 202 can include an access needle ("needle") 204 supported by a needle hub 203. In an embodiment, the obturator assembly 102 includes an elongate obturator body ("obturator") 104. As used herein, an obturator 104 includes an elongate medical device configured to be disposed within a lumen of a needle and to prevent bone fragments, tissue, or the like from entering the needle lumen. Advantageously, the obturator prevents tissues from obstructing a fluid flow through the needle lumen, after the needle has been placed to access the medullary cavity 90. As will be appreciated, in some embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, and the like. Accordingly, the obturator assembly 102 may be referred to more generally as an elongated medical instrument assembly. In like manner, the obturator 104 may be referred to more generally as an elongated medical instrument.

In an embodiment, the obturator assembly 102 includes a coupling hub 103 that is attached to the obturator 104 in any suitable manner (e.g., one or more adhesives or overmolding). The coupling hub 103 can be configured to interface with the driver 101. The coupling hub 103 may alternatively be referred to as an obturator hub 103 or, more generally, as an elongated instrument hub 103. In an embodiment, the shield 105 is configured to couple with the obturator 104 to prevent accidental needle stick injuries when the obturator is removed after placement of the needle 204.

In an embodiment, the needle assembly 202 includes a needle 204. However, in some embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula. In an embodiment, the needle assembly 202 includes a needle hub 203 that is attached to the needle 204 in any suitable manner. The needle hub 203 can be configured to couple with the obturator hub 103 and may thereby be coupled with the driver 101. The needle hub 203 may alternatively be referred to as a cannula hub 203. In an embodiment, a cap 107 may be provided to cover at least a distal portion of the needle 204 and the obturator 104 prior to use of the access assembly 109. For example, in an embodiment, a proximal end of the cap 107 can be coupled to the obturator hub 103.

Figure 1B:
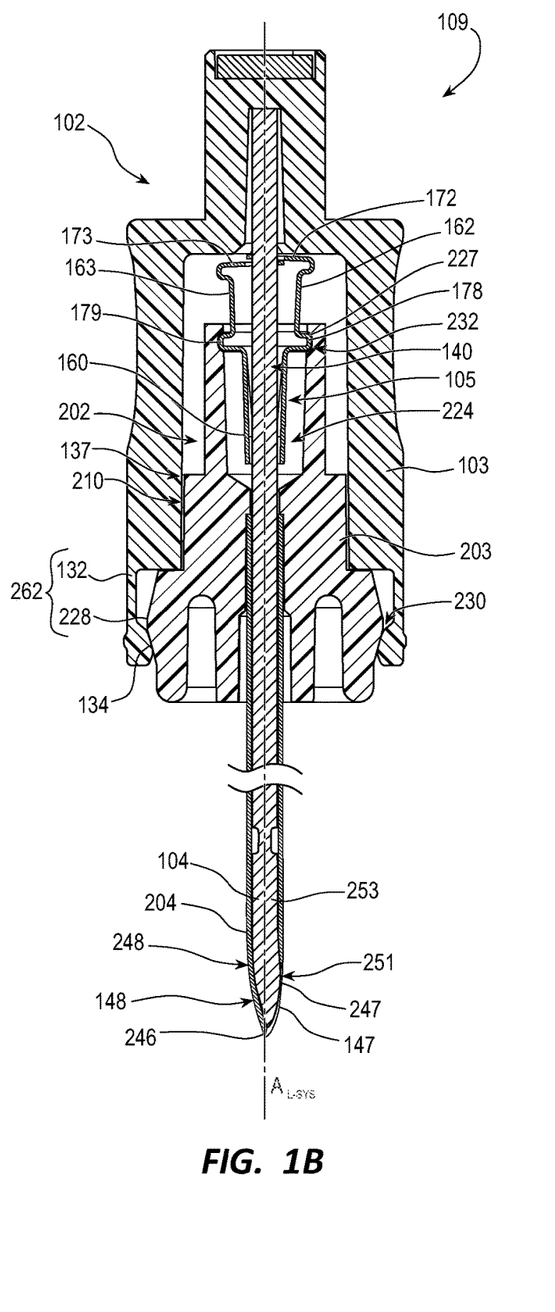
FIG. 1B shows a cross-sectional view of an access assembly, in accordance with embodiments disclosed herein.
Figure 1C:
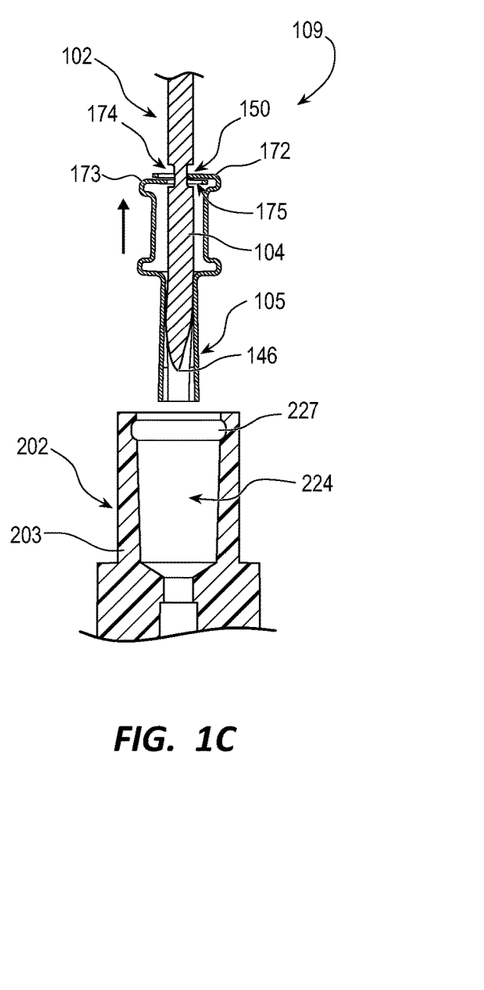
FIG. 1C shows a cross-sectional view of an obturator tip and a safety shield in a locked position and removed from the access assembly of FIG. 1B, in accordance with embodiments disclosed herein.
Figure 1D:
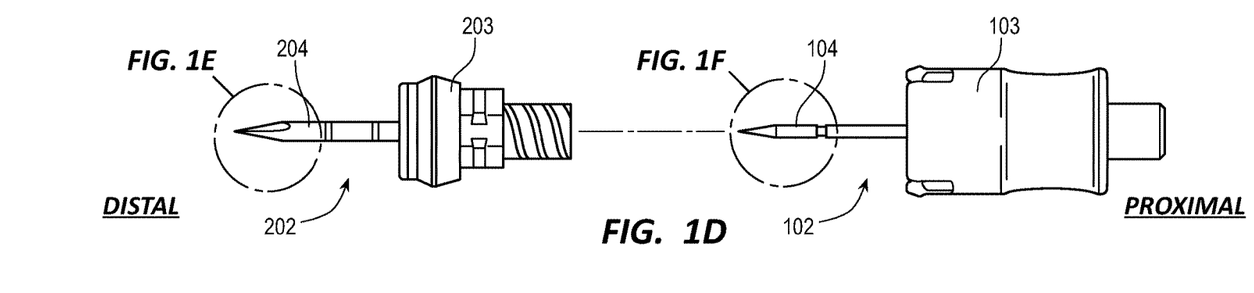
FIGS. 1D-1F show close up detailed views of the access assembly of FIG. 1B, in accordance with embodiments disclosed herein.
Figures 1E, 1F:
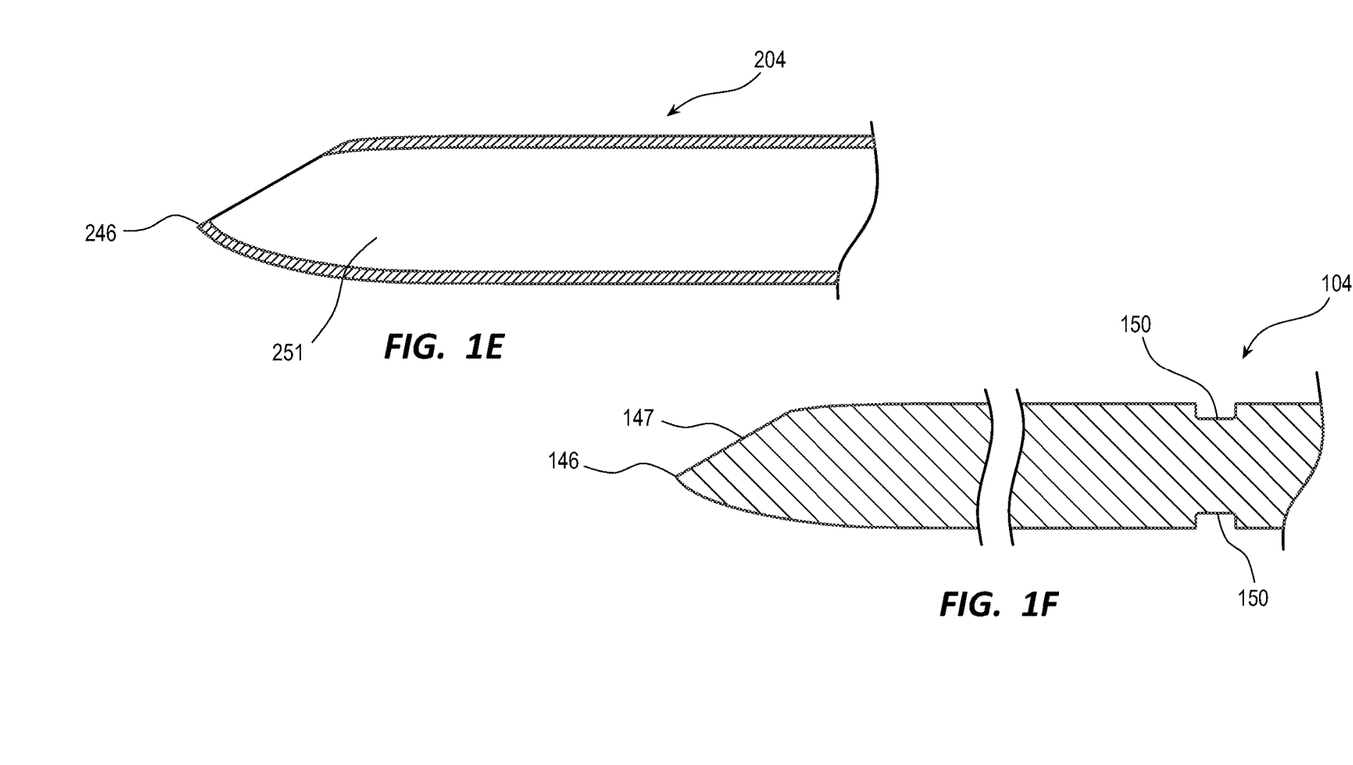

FIGS. 1B-1F show further details of the access assembly 109. FIG. 1B shows a cross-sectional view of the access assembly 109 with the needle hub 203 retained by the obturator hub 103. The obturator 104 is disposed within the needle and the shield 105 is in the unlocked position within the access assembly 109. FIG. 1C shows a cross-sectional view of the access assembly 109 with the obturator 104 removed from the needle and the shield in the second, locked operational mode. FIG. 1D shows an exploded view of the access assembly 109. FIG. 1E shows a close up, cross-sectional view of a distal portion of the needle 204. FIG. 1F shows a close up, cross-sectional view of a distal portion of the obturator 104. In an embodiment, as the obturator 104 is withdrawn from the needle lumen 251, the shield 105 can engage recesses 150 to lock the shield 105 relative to the obturator tip 146 to prevent accidental needle stick injuries.

As discussed herein, the obturator 104 can be formed of any suitable material to inhibit tissue and/or bone from entering a lumen of the needle 204 during an access event. Exemplary materials can include, but not limited to, metal, alloys, stainless steel, copper, aluminum, titanium, plastics, polymer, thermoplastic, electrically conductive thermoplastics, combinations thereof, or the like.

With continued reference to FIG. 1A, the driver 101 may take any suitable form. The driver 101 may include a handle 110 that may be gripped by a single hand of a user. In an embodiment, the driver 101 further includes a coupling interface 112, which is formed as a socket 113 that defines a cavity 114. The coupling interface 112 can be configured to couple with the obturator hub 103. In an embodiment, the socket 113 includes sidewalls that substantially define a hexagonal cavity into which a hexagonal protrusion of the obturator hub 103 can be received. Other suitable connection interfaces are also contemplated.

The driver 101 can include an energy source 115 of any suitable variety that is configured to energize the rotational movement of the coupling interface 112 and provide a motive force. For example, in some embodiments, the energy source 115 may comprise one or more batteries that provide electrical power for the driver 101. In some embodiments, the energy source 115 can comprise one or more springs (e.g., a coiled spring, flat spring, or the like) or other biasing member that may store potential mechanical energy that may be released upon actuation of the driver 101.

The energy source 115 may be coupled with the coupling interface 112 in any suitable manner. For example, in an embodiment, the driver 101 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage to the gear assembly 117. The driver 101 can include a mechanical coupling of any suitable variety to couple the gear assembly 117 with the coupling interface 112. In other embodiments, the gear assembly 117 may be omitted.

Further details and embodiments of the intraosseous access system 100 can be found in WO 2018/075694, WO 2018/165334, WO 2018/165339, and US 2018/0116693, each of which is incorporated by reference in its entirety into this application.

In an embodiment, the system 100 can include a sensing obturator 304 supported by an obturator hub 303 and configured to be coupled to an access assembly 109 and driver 101, as described herein. Exemplary embodiments of sensing obturators 304 are shown in FIGS. 2A-4. The sensing obturator 304 can include one or more sensors, e.g. sensor 310, disposed proximate a distal tip 146 of the obturator. In an embodiment, the sensor 310 can be disposed on a beveled distal surface 147 of the sensing obturator 304 and can contact a tissue of the patient during an access event.

In an embodiment, the sensor 310 can be configured to detect a change in modality to determine if a distal tip 346 of the obturator 304, and thereby a distal tip 246 of the needle 204, has accessed a medullary cavity 90. Exemplary modalities can include, but not limited to, pressure, oxygen saturation, electrical impedance, temperature, pH, combinations thereof, or the like, as described in more detail herein.

Figure 2A:
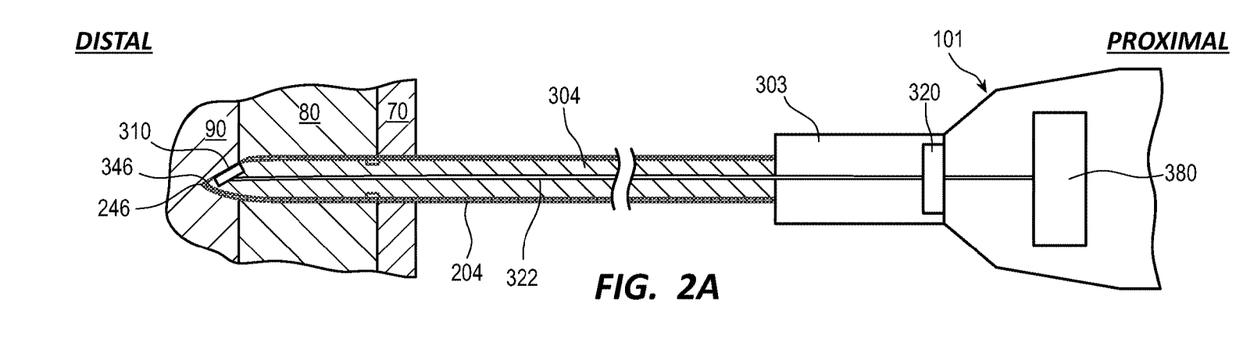
FIGS. 2A-2C show various embodiments of a sensing obturator, in accordance with embodiments disclosed herein.

In an embodiment, the sensing obturator 304 can include a sensor interface 320 disposed at a proximal end thereof. In an embodiment, as shown in FIG. 2A, the sensor 310 and the sensor interface 320 can be communicatively coupled by way of a wire 322 extending axially through the sensing obturator 304. In an embodiment, the wire 322 can be coextruded with the sensing obturator 304. In an embodiment, the wire 322 can extend through a lumen defined by the obturator 304.

Figure 2B:
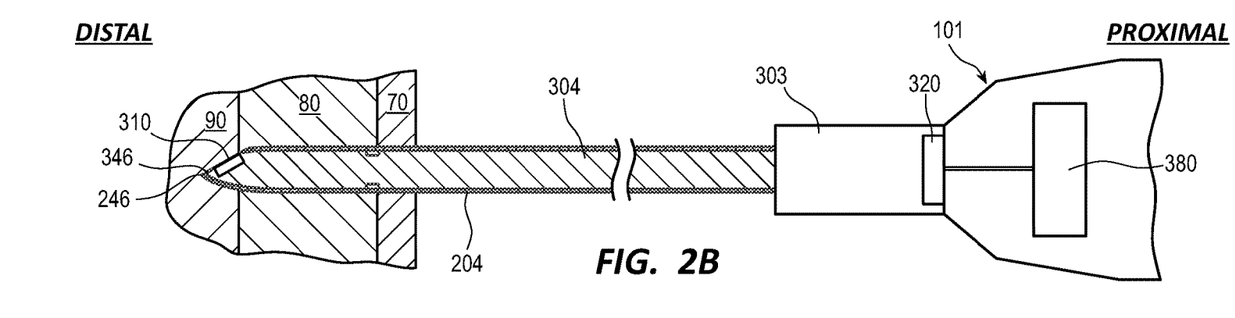

In an embodiment, as shown in FIG. 2B, the obturator 304 can be formed of a conductive material, for example an electrically conductive polymer, fiber optically conductive thermoplastic, combinations thereof, or the like. As such, an input that is detected by the sensor 310 can be communicated to the sensor interface 320 through the body of the sensing obturator 304 itself. In an embodiment, the sensing obturator 304 can be formed of a conductive material that also displays flexible characteristics to mitigate needle stick injuries. For example, the obturator 304, when disposed within the needle lumen 251, can display sufficient compressive strength to prevent tissue entering the needle lumen 251 during an access event. Further, when removed from the needle lumen 251, the obturator 304 can display sufficient flexible characteristics to deform when a force applied and mitigate needle stick injuries. Further details and embodiments can be found in U.S. patent application Ser. No. 17/183,820, filed Feb. 24, 2021, which is incorporated by reference in its entirety into this application.

In an embodiment, the sensor interface 320 can be configured to communicatively couple with a control logic 380 disposed within the driver 101. In an embodiment, the sensor interface 320 can be both rotatably and communicatively coupled with the driver 101 to allow the access assembly 109, with the sensing obturator 304 disposed therein, to rotate relative to the driver 101, while maintaining a communicative coupling therebetween. As used herein, the control logic 380 can include one or more processor(s), storage, communications logic, and the like, configured to receive information from the one or more sensors 310, determine if a distal tip 246 of the needle 204 has accessed a medullary cavity 90, and modify the activation of the driver 101. In an embodiment, the reusable components, e.g. control logic 380, associated components, etc., can be disposed within the reusable drill 101. As such only the sensor 310 is disposed within the single-use sensing obturator 304, and is configured to communicate with the reusable components disposed within the drill 101. Advantageously, the cost and complexity of the disposable components, i.e. the obturator 304, are mitigated.

In an embodiment, a sensor 310 can include a pressure transducer configured to detect a change in compressive force applied to a proximal end of the sensing obturator 304 and provide a signal to the sensing interface 320. The sensing interface 320 in turn provides the signal to the control logic 380 that detects and interprets the pressure transducer signal. Where a pressure transducer signal indicates a relatively high pressure level, the control logic 380 can determine the needle tip 246 and obturator tip 346 are disposed within the relatively hard bone cortex 80. Where a pressure transducer signal indicates a decrease in relative pressure level, the control logic 380 can determine the needle tip 246 and obturator tip 346 has passed through the bone cortex 80 and accessed the relatively soft tissue disposed within the medullary cavity 90. As such, the control logic 380 can automatically stop the electric motor 116 to indicate to the user that the medullary cavity 90 has been accessed, and/or to prevent backwalling.

In an embodiment, a sensor 310 can include an oxygen saturation sensor configured to detect a change in oxygen saturation of the tissue that is in contact with a distal tip of the sensing obturator 304 and provide a signal to the sensing interface 320. The sensing interface 320 in turn provides the signal to the control logic 380 that detects and interprets the oxygen saturation signal. Where a signal indicates a relatively low oxygen saturation level, the control logic 380 can determine the needle tip 246 and obturator tip 346 are disposed within the bone cortex 80. Where a signal indicates an increase in relative oxygen saturation level, the control logic 380 can determine the needle tip 246 and obturator tip 346 has passed through the bone cortex 80 and accessed the relatively oxygenated tissue disposed within the medullary cavity 90. As such, the control logic 380 can automatically stop the electric motor 116 to indicate to the user that the medullary cavity 90 has been accessed, and/or to prevent backwalling.

In an embodiment, a sensor 310 can include an electrical impedance sensor configured to detect a change in electrical impedance of the tissue that is in contact with a distal tip of the sensing obturator 304 and provide a corresponding change in signal to the sensing interface 320. The sensing interface 320 in turn provides the signal to the control logic 380 disposed within drill 101, which detects and interprets the electrical impedance signal. Where a signal indicates a first electrical impedance, the control logic 380 can determine the needle tip 246 and obturator tip 346 are disposed within the bone cortex 80. Where a signal indicates a change in electrical impedance to a second electrical impedance level, the control logic 380 can determine the needle tip 246 and obturator tip 346 has passed through the bone cortex 80 and accessed the tissue disposed within the medullary cavity 90. As such, the control logic 380 can automatically stop the electric motor 116 to indicate to the user that the medullary cavity 90 has been accessed, and/or to prevent backwalling. These and other modalities as also contemplated, including sensors configured to detect changes in temperature, pH, or the like that can be employed to determine when the needle tip 251 has accessed the medullary cavity 90.

Figure 2C:
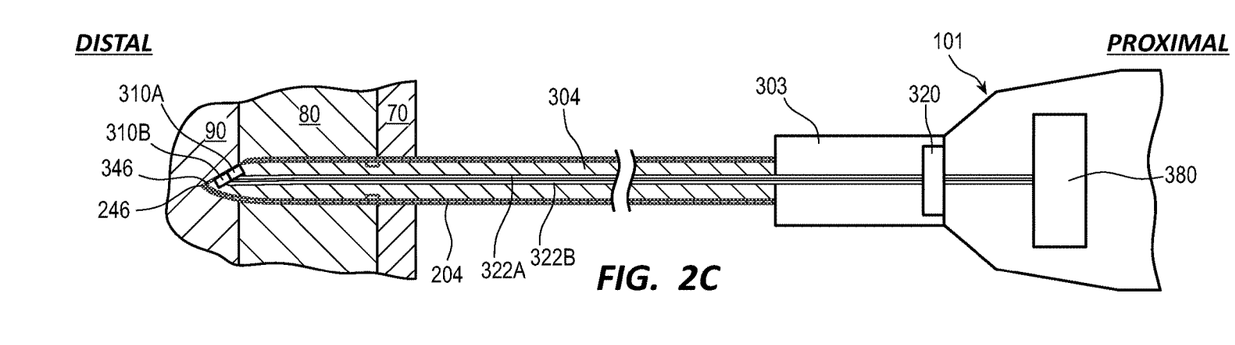

As shown in FIG. 2C, the sensing obturator can include two or more sensors 310, e.g. a first sensor 310A and a second sensor 310B, each configured to detect a different modality such pressure, oxygen saturation, electrical saturation, temperature, pH, combinations thereof, or the like. Advantageously, the control logic 380 can receive information the two or more sensors 310A, 310B to provide increased accuracy as to when the needle tip 251 has passed through the bone cortex 80 and accessed the medullary cavity 90. The first sensor 310A and the second sensor 310B can be communicatively coupled to the sensor interface 320 via wires 322A and 322B, respectively.

Figure 3A:
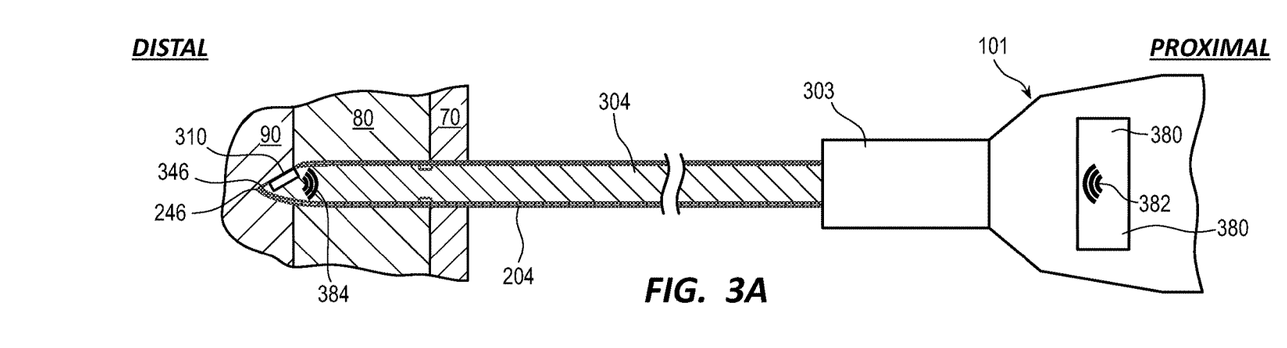
FIGS. 3A-3B show various embodiments of a sensing obturator, in accordance with embodiments disclosed herein.

As shown in FIG. 3A, in an embodiment, the sensor 310 and the control logic 380 can be communicatively coupled by way of wireless communication. Exemplary wireless communication modalities can include WiFi, Bluetooth, Near Field Communications (NFC), electromagnetic (EM), radio frequency (RF), combinations thereof, or the like. In an embodiment, the control logic 380 can include a communication logic configured to provide an interrogation signal 382. The sensor 310 can include a passive RFID chip configured to activate in the presence or absence of a given modality, or change in modality, as described herein. For example a drop in pressure, an increase in oxygen saturation, a change in relative electrical impedance, combinations thereof, or the like. As such, when sensor 310 is activated, the interrogation signal 382 can induce the sensor 310 to provide a response signal 384 that can be detected and interpreted by the control logic 380 to determine that the obturator tip 346 and as such a needle tip 246 has accessed the medullary cavity 90, as described herein.

Figure 3B:
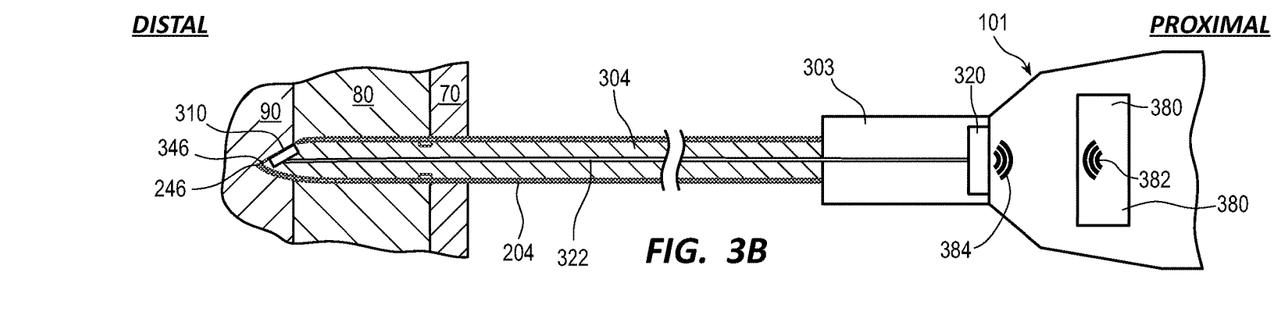

In an embodiment, as shown in FIG. 3B, a sensor 310 can be communicatively coupled with a sensor interface 320 by either a wired coupling 322 or by a conductive obturator body 304, as describe herein. The interface 320 can include a passive RFID chip and when the sensor 310 detects a change in modality that indicates the medullary cavity 90 has been accessed, signals communicated to the sensor interface 320 can activate an RFID chip causing the RFID chip to be responsive to an interrogation signal 382. The interrogation 382 can then induce the RFID to provide a response signal 384 that can be detected and interpreted by the control logic 380, as described herein.

Figure 4:
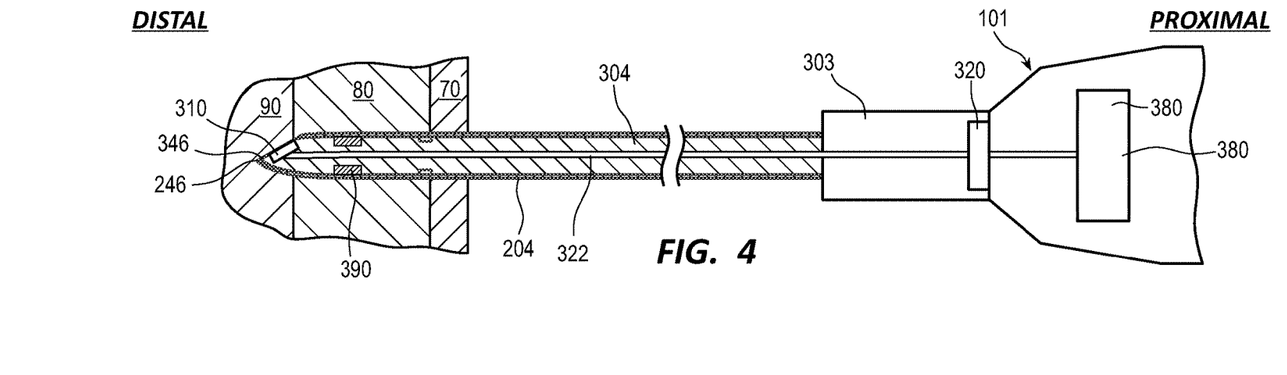
FIG. 4 shows an embodiment of a sensing obturator, in accordance with embodiments disclosed herein.

In an embodiment, as shown in FIG. 4 a distal portion of the obturator 304 can include a marker 390, configured to be detected by a tracking system. In an embodiment the marker 390 can be a passive magnet configured to be detected by a multi-modal tracking system that can use magnetic, electromagnetic, ultrasonic modalities, combinations thereof, or the like. Details of exemplary tracking systems configured to detect the marker 390 can be found in U.S. Pat. Nos. 8,388,541, 8,781,555, 8,849,382, 9,445,743, 9,456,766, 9,492,097, 9,521,961, 9,554,716, 9,636,031, 9,649,048, 10,159,531, 10,172,538, 10,413,211, 10,449,330, U.S. Publication Nos. 2014/0031674, 2014/0188133, 2015/0080762, and U.S. Publication No. 2018/0116551, each of which are incorporated by reference in their entirety into this application. Advantageously, the obturator 304 with the marker 390, and the needle tip 246, could be detected and tracked using a tracking system to facilitate determining access to the medullary cavity 90.

As will be appreciated although embodiments are described herein in terms of sensing obturators of an intraosseous access system 100, embodiments of sensing obturators, elongate medical devices, and the like can also be used with various medical device systems configured to access an interior portion of a patient, e.g. ultrasound systems, medical device tracking systems, catheter systems, or similar electronic devices. Accordingly, sensing obturators and the like can be used to detect changes in modalities and modify operation of the medical device systems, or provide alerts, to indicate access to the target area has been achieved.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An obturator assembly configured for use with an intraosseous access system, comprising:
    an elongate obturator body; and
    an electrical impedance sensor disposed proximate a distal end of the obturator body, the electrical impedance sensor configured to detect a change in modality to determine access to a medullary cavity, the electrical impedance sensor communicatively coupled with a control logic disposed in a driver of the intraosseous access system, the control logic configured to modify operation of the driver when the electrical impedance sensor detects the change in modality, the electrical impedance sensor further including an RFID chip, wherein the change in modality detected by the electrical impedance sensor transitions the RFID chip from an inactive state to an active state and, wherein the control logic is configured to provide an interrogation signal configured to induce a response signal from the RFID chip in the active state to determine access to the medullary cavity.

2. The obturator assembly according to claim 1, wherein the obturator body further includes a sensor interface disposed at a proximal end of a hub of the obturator body, the sensor interface configured to both rotatably and communicatively couple the electrical impedance sensor with the control logic.

3. The obturator assembly according to claim 2, wherein the obturator body includes one of an electrically conductive or an optically conductive thermoplastic configured to communicatively couple the electrical impedance sensor with the sensor interface.

4. The obturator assembly according to claim 2, wherein the obturator body includes a wire extending axially therethrough to communicatively couple the electrical impedance sensor with the sensor interface.

5. The obturator assembly according to claim 1, wherein the obturator body is configured to be disposed within a needle, and wherein the electrical impedance sensor is disposed proximate a distal end of the needle.

6. The obturator assembly according to claim 1, wherein the obturator body further includes a second sensor configured to detect a second modality configured to determine access to the medullary cavity.

7. The obturator assembly according to claim 6, wherein the second sensor is selected from a group consisting of a pressure transducer, an oxygen saturation sensor, a temperature sensor, and a pH sensor.

8. A method of detecting access to a medullary cavity, comprising:
    providing an elongate obturator body including an electrical impedance sensor disposed at a distal end of the obturator body;
    urging the elongate obturator body through a bone cortex;
    detecting a first electrical impedance modality level;
    accessing the medullary cavity;
    detecting a change in modality level from the first electrical impedance modality level to determine access to the medullary cavity; and
    communicating the change in modality level to a control logic, wherein the electrical impedance sensor further includes an RFID chip configured to transition between an active state and an inactive state, and wherein detecting the change in modality level transitions the RFID chip to the active state and, wherein, the control logic provides an interrogation signal configured to induce a response signal from the RFID chip in the active state and determines access to the medullary cavity.

9. The method according to claim 8, wherein the elongate obturator body is disposed within an intraosseous access needle.

10. The method according to claim 8, wherein the control logic is disposed within an intraosseous access driver releasably coupled to the elongate obturator body.

11. The method according to claim 10, further including modifying an operation of the intraosseous access driver by the control logic when the electrical impedance sensor detects the change in modality level.

12. The method according to claim 10, wherein the obturator body further includes a sensor interface disposed at a proximal end thereof and configured to engage the intraosseous access driver and communicatively and rotatably couple the electrical impedance sensor and the control logic.

13. The method according to claim 12, wherein the obturator body includes an electrically conductive thermoplastic configured to communicatively couple the electrical impedance sensor with the sensor interface.

14. The method according to claim 12, wherein the obturator body includes a wire extending axially therethrough and configured to communicatively couple the electrical impedance sensor with the sensor interface.

15. The method according to claim 8, further including detecting a change in a second modality level to determine access to the medullary cavity and communicating the change in the second modality level to the control logic.

16. The method according to claim 15, wherein the second modality level is selected from a group consisting of a pressure, an oxygen saturation, a temperature and a pH.

\* \* \* \* \*